United States Patent
Kurashima et al.

(10) Patent No.: US 12,159,076 B2
(45) Date of Patent: Dec. 3, 2024

(54) DEVICE FOR DIAGNOSING BRAIN DISEASE

(71) Applicant: NATSUME RESEARCH INSTITUTE, CO., LTD., Tokyo (JP)

(72) Inventors: Wataru Kurashima, Tokyo (JP); Kouichi Kikuchi, Tokyo (JP)

(73) Assignee: Natsume Research Institute, Co., Ltd., Tokyo (JP)

( * ) Notice: Subject to any disclaimer, the term of this patent is extended or adjusted under 35 U.S.C. 154(b) by 463 days.

(21) Appl. No.: 17/414,333

(22) PCT Filed: Dec. 13, 2019

(86) PCT No.: PCT/JP2019/048894
§ 371 (c)(1),
(2) Date: Jun. 16, 2021

(87) PCT Pub. No.: WO2020/129834
PCT Pub. Date: Jun. 25, 2020

(65) Prior Publication Data
US 2022/0054076 A1 Feb. 24, 2022

(30) Foreign Application Priority Data
Dec. 17, 2018 (JP) .................. 2018-235105

(51) Int. Cl.
*G06F 3/14* (2006.01)
*G06T 7/00* (2017.01)
(Continued)

(52) U.S. Cl.
CPC .............. *G06F 3/14* (2013.01); *G06T 7/0016* (2013.01); *G06T 7/62* (2017.01); *G06V 40/19* (2022.01);
(Continued)

(58) Field of Classification Search
CPC .......... G06F 3/14; G06T 7/62; G06T 7/0016; G06V 40/19
See application file for complete search history.

(56) References Cited

U.S. PATENT DOCUMENTS

2009/0312817 A1* 12/2009 Hogle .................... A61B 5/682
607/54
2010/0085539 A1 4/2010 Harada et al.
(Continued)

FOREIGN PATENT DOCUMENTS

| JP | 2002-34920 A | 2/2002 |
| JP | 2002-282208 A | 10/2002 |

(Continued)

OTHER PUBLICATIONS

Extended European Search Report for EP application No. 19900976.2 dated Jul. 20, 2022 (9 pages).
(Continued)

*Primary Examiner* — Kevin Ky
(74) *Attorney, Agent, or Firm* — Pyprus Pte Ltd; George D. Liu (57) ABSTRACT

To provide a device which can diagnose a brain disease by observing a pupil diameter. A device for diagnosing a brain disease, equipped with a display image control section (3), an imaging section (5) and a judgment section (7), wherein the display image control section (3) can vary a display image displayed on a display section on the basis of a first pattern, the imaging section (5) can take an image of the pupil of a user who watches the display image, and the judgment section (7) can determine whether or not the user is affected with a brain disease using a pattern of the time-dependent change in the size of the pupil of the user which is imaged by the imaging section and the first pattern.

9 Claims, 6 Drawing Sheets

(51) Int. Cl.
  *G06T 7/62* (2017.01)
  *G06V 40/19* (2022.01)
(52) U.S. Cl.
  CPC .............. *G06T 2207/30041* (2013.01); *G06V 2201/03* (2022.01)

(56) References Cited

U.S. PATENT DOCUMENTS

| | | | |
|---|---|---|---|
| 2016/0166133 A1* | 6/2016 | Chiba | A61B 1/00009 600/109 |
| 2017/0135577 A1* | 5/2017 | Komogortsev | A61B 5/168 |
| 2017/0232118 A1* | 8/2017 | Braithwaite | A61K 35/16 424/9.2 |
| 2017/0249433 A1* | 8/2017 | Hagen | G16H 10/60 |
| 2018/0064744 A1* | 3/2018 | Cohen | A61P 25/00 |
| 2018/0110839 A1* | 4/2018 | Bell | A61K 35/16 |
| 2018/0190011 A1* | 7/2018 | Platt | G02B 27/017 |
| 2018/0232799 A1* | 8/2018 | Kitagawa | G06Q 30/0623 |
| 2018/0249941 A1* | 9/2018 | Liston | A61B 3/0041 |
| 2018/0276883 A1* | 9/2018 | D'Alessandro | G06T 11/60 |
| 2018/0298102 A1* | 10/2018 | Wyss-Coray | A61K 31/7088 |
| 2018/0311280 A1* | 11/2018 | Braithwaite | A61K 38/385 |
| 2018/0353578 A1* | 12/2018 | Wyss-Coray | A61P 25/28 |
| 2019/0024091 A1* | 1/2019 | Wyss-Coray | C07K 16/28 |
| 2019/0105314 A1* | 4/2019 | Braithwaite | A61K 9/2866 |
| 2019/0246969 A1* | 8/2019 | Thomas | A61B 3/0025 |
| 2019/0282086 A1* | 9/2019 | Cohen | A61B 3/0025 |
| 2019/0313967 A1* | 10/2019 | Lee | A61F 5/02 |
| 2021/0011545 A1* | 1/2021 | Min | H04M 1/72409 |
| 2022/0054076 A1* | 2/2022 | Kurashima | G06F 3/14 |

FOREIGN PATENT DOCUMENTS

| | | |
|---|---|---|
| JP | 2002-541959 A | 12/2002 |
| JP | 2003-70753 A | 3/2003 |
| JP | 2016-504089 A | 2/2016 |
| JP | WO2017057631 A1 | 4/2017 |
| JP | 2017-184996 A | 10/2017 |
| WO | WO2018/203828 A1 | 11/2018 |

OTHER PUBLICATIONS

F. Fotiou et al., Automated standardized pupillometry with optical method for purposes of clinical practice and research, Clinical Physiology, vol. 20, No. 5, Sep. 1, 2000, pp. 336-347.

International Search Report of International Patent Application No. PCT/JP2019/048894 completed Feb. 10, 2020 and mailed Feb. 25, 2020 (5 pages).

Written Opinion of International Patent Application No. PCT/JP2019/048894 completed Feb. 10, 2020 and mailed Feb. 25, 2020 (4 pages).

* cited by examiner

DEVICE FOR DIAGNOSING BRAIN DISEASE

TECHNICAL FIELD

This invention relates to a device for diagnosing a brain disease. More specifically, this invention relates to a device for diagnosing a brain disease that diagnoses whether a user has a brain disease using changes in the user's pupil when the user sees a pattern video.

BACKGROUND ART

International Publication No. WO2017-057631 pamphlet discloses a viewer's feeling determination device. The device disclosed in this publication can be used to determine the feeling of a user by photographing the user's pupil while eliminating the effects of the user's breathing, the brightness and darkness of the environment, and the user's pulse.

There has been a demand for the development of a novel device using a device that can photograph the user's pupil, such as the device described above.

CITATION LIST

Patent Literature

PTL 1: International Publication No. WO2017-057631 pamphlet

SUMMARY OF THE INVENTION

Technical Problem

An object of this invention is to provide novel use of a device that can observe the pupil. Specifically, an object of this invention is to provide a device that can diagnose a brain disease by observing the pupil diameter.

Solution to Problem

The present invention is basically based on the finding that changes in a pupil of a user with brain damage when a display image is changed are different from those of a healthy person.

One of the embodiments disclosed in this specification (first embodiment) relates to a device for diagnosing a brain disease.

The device for diagnosing a brain disease 1 has a display image control unit 3, a photographing unit 5, and a determination unit 7.

The display image control unit 3 is an element for changing a display image displayed on a display unit based on a first pattern.

The photographing unit 5 is an element for photographing a pupil of a user who visually recognizes the display image.

The determination unit 7 is an element for determining whether the user has a brain disease using a pattern of time-dependent changes in size of the pupil of the user photographed by the photographing unit and the first pattern.

In the device for diagnosing a brain disease 1, the display image control unit 3 changes the display image displayed on the display unit based on the previously stored first pattern. Then, the photographing unit 5 photographs the pupil of a user who visually recognizes the display image.

The determination unit 7 receives an image including the user's pupil photographed by the photographing unit 5. Then, the determination unit 7 obtains a pattern of time-dependent changes in the size of the pupil of the user photographed by the photographing unit, and determines whether the user has a brain disease using the pattern of time-dependent changes and the first pattern. For example, when there is a correlation between the pattern of time-dependent changes in the pupil size of the user and the first pattern, the user may be determined to be a healthy person. The pattern of time-dependent changes in the pupil size of the user preferably includes a pattern of time-dependent changes in the difference of the pupil size between a dominant eye and a non-dominant eye.

This device may be a device for diagnosing a brain disease, comprising:
a display image control unit that changes a display image displayed on a display unit based on a first pattern that varies based on a predetermined time pattern;
a photographing unit that photographs a pupil of a user who visually recognizes the display image; and a determination unit that determines whether the user has a brain disease using information relating to a pattern of time-dependent changes in size of the pupil of the user photographed by the photographing unit and relating to the predetermined time pattern of the first pattern.

The first pattern is, for example, one or two or more of luminance, color, and lightness that vary based on the predetermined time pattern.

A specific example of the first pattern includes a white screen and a black screen that change periodically. This device preferably further comprises an age memory unit that stores age information of the user. Then, the display image control unit 3 preferably controls the predetermined time pattern based on the age information of the user stored in the age memory unit.

The brain disease is, for example, epilepsy, neurodegenerative disease, neural stem cell disease, neural progenitor cell disease, ischemic disease, neurological trauma, affective disorder, neuropsychiatric disease, retinal degenerative disease, retinal injury/trauma, cognitive, learning and memory impairment, Alzheimer's disease, mild cognitive impairment (MCI), Parkinson's disease, parkinsonian syndrome, Huntington's disease, amyotrophic lateral sclerosis, ischemic stroke, traumatic brain injury, depression, bipolar depression/disorder, chronic fatigue syndrome, anxiety syndrome/disorder, autism, or Asperger's syndrome. This device is preferably a device for diagnosing a brain disease that diagnoses the brain disease according to a machine-learning prediction algorithm.

Advantageous Effects of the Invention

This invention can provide a device that can diagnose whether a user has a brain disease, whether the brain disease is severe, and whether the risk of developing the brain disease is high, only by using a relatively simple device (e.g., a device that can photograph the pupil, and a computer).

BRIEF DESCRIPTION OF THE DRAWINGS

FIG. 1-1 is a conceptual diagram for explaining the configuration of a device for diagnosing a brain disease.

FIG. 1-2 is a conceptual diagram for explaining the configuration of a device for diagnosing a brain disease.

FIG. 2(a) shows an example in which a white screen and a black screen are alternately displayed at regular intervals. FIG. 2(b) shows an example in which a white screen, a video screen, and a predetermined luminance screen are displayed in a certain pattern.

FIG. 3(a) is a conceptual diagram showing pupil changes in a healthy person and a pattern display. On the other hand, FIG. 3(b) is a conceptual diagram showing pupil changes in a patient with Parkinson's disease and a pattern display.

FIG. 11 shows graphs that replace drawings showing pupil changes.

DESCRIPTION OF THE EMBODIMENTS

Modes for carrying out the present invention will be described below with reference to the drawings. The present invention is not limited to the modes described below, and includes those appropriately modified by a person skilled in the art within a scope obvious from the following modes.

One of the embodiments disclosed in this specification (first embodiment) relates to a device for diagnosing a brain disease. The device for diagnosing a brain disease is a device using a computer for determining one or more of whether the user has a brain disease, whether the brain disease is severe, and whether the risk of developing the brain disease is high.

Examples of brain diseases include epilepsy, neurodegenerative disease, neural stem cell disease, neural progenitor cell disease, ischemic disease, neurological trauma, affective disorder, neuropsychiatric disease, retinal degenerative disease, retinal injury/trauma, cognitive, learning and memory impairment, Alzheimer's disease, mild cognitive impairment (MCI), Parkinson's disease, parkinsonian syndrome, Huntington's disease, amyotrophic lateral sclerosis, ischemic stroke, traumatic brain injury, depression, bipolar depression/disorder, chronic fatigue syndrome, anxiety syndrome/disorder, autism, or Asperger's syndrome.

Figure 11:
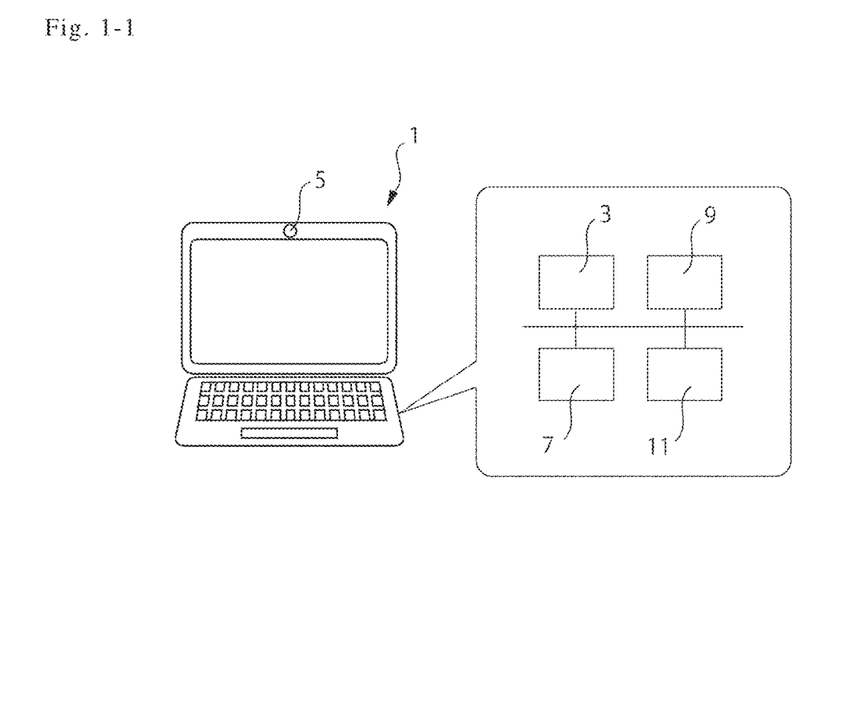

FIG. 1-1 is a conceptual diagram for explaining the configuration of a device for diagnosing a brain disease. As shown in FIG. 1-1, the device for diagnosing a brain disease 1 has a display image control unit 3, a photographing unit 5, and a determination unit 7. The display image control unit 3 is an element for changing a display image displayed on a display unit based on a first pattern. Examples of the display unit include a monitor, a screen, and a wall for projection.

This device can be implemented by a computer that is capable of exchanging information with a photographing device, such as a camera. Photographing information obtained by a camera or the like may be input to the computer through a cable or the like. The photographing information may also be input to the computer by radio. The computer comprises an input/output unit, a control unit, a calculation unit, and a memory unit, and each element is configured to be able to deliver and receive information by bus or the like. The computer stores the input information in the memory unit. Further, the control unit of the computer reads a control program stored in the memory unit, and allows the calculation unit to perform various calculations using the input information and information stored in the memory unit. Then, the calculation results are appropriately stored in the memory unit and appropriately output through the input/output unit.

The first pattern is, for example, one or two or more of luminance, color, and lightness that vary based on a predetermined time pattern. When the pattern includes two types of images (videos), the frequency of switching is, for example, 1 second or more and 10 seconds or less, and may be 2 seconds or more and 6 seconds or less, or 2 seconds or more and 5 seconds or less. Switching may be made at regular intervals. Further, the first screen (e.g., white screen) and the second screen (e.g., black screen) may be switched every different number of seconds. This pattern may be such that, for example, three or more screens are switched.

Figure 2:
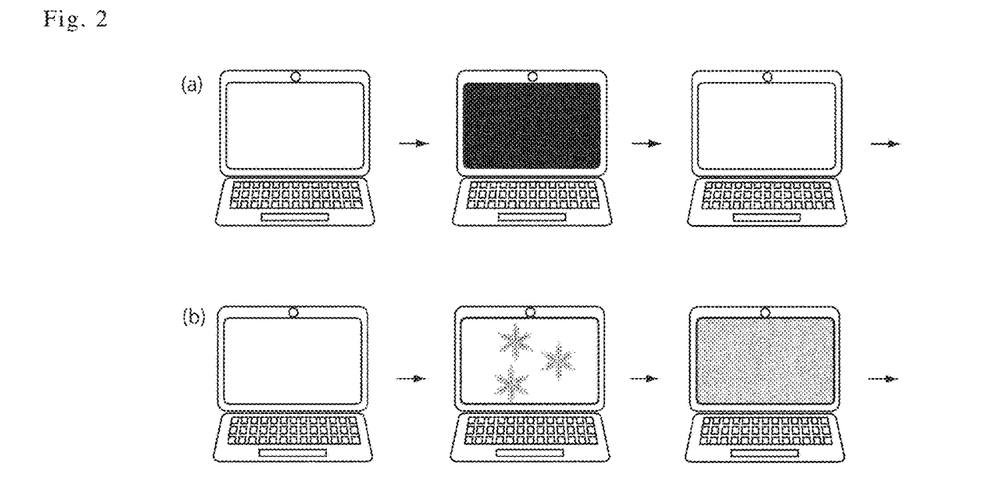
FIG. 2 shows conceptual diagrams showing examples of a first pattern.

FIG. 2 shows conceptual diagrams showing examples of a first pattern. FIG. 2(a) shows an example in which a white screen and a black screen are alternately displayed at regular intervals. FIG. 2(b) shows an example in which a white screen, a video screen, and a predetermined luminance screen are displayed in a certain pattern.

The photographing unit 5 is an element for photographing the pupil of a user who visually recognizes a display image. Since International Publication No. WO2017-057631 pamphlet (PTL 1) discloses a pupil diameter measuring instrument including a photographing unit, such as a camera, such a pupil diameter measuring instrument may be used.

Figure 12:
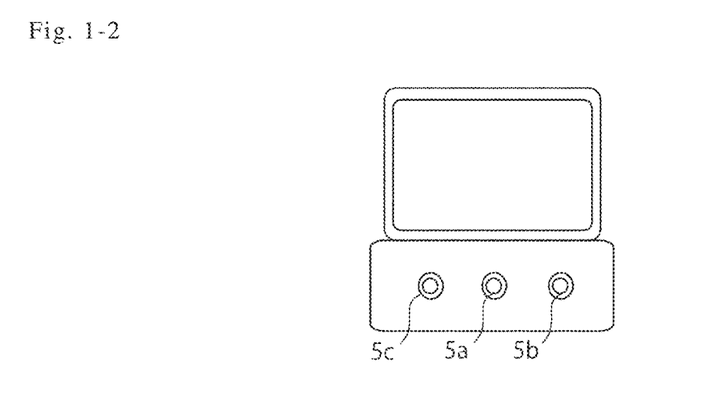

FIG. 1-2 is a conceptual diagram for explaining the configuration of a device for diagnosing a brain disease. The photographing unit 5 contains three photographing elements. This example contains a central camera (photographic element) 5a and cameras (photographic elements) 5b and 5c at both ends. In this example, the cameras 5b and 5c track and capture one of the eyeballs by image recognition, and the distance from the camera 5a in the middle of the cameras 5b and 5c to the eyeball is calculated by triangulation using the distance between the cameras 5b and 5c, and the angle to the eyeball. Since the pupil diameter photographed by the camera 5a varies with the distance, the measured pupil diameter photographed by 5a is corrected by the distance from 5a. As a result, the exact pupil diameter can be determined even if the face moves a little.

The pupil is the area in the center of the eyeball that allows light to pass through. The size of the pupil changes under the influence of light and other factors. On the other hand, the color of the pupil is different from the iris in the periphery of the pupil. Therefore, a plurality of eyeball images of a user is taken, the area where the size changes is analyzed, and the color (color width) of the area is stored. In this way, the pupil color of the user can be stored. Then, a video image including the user's pupil is taken, and the color is analyzed. As a result, there is a continuous color region. Of the region, a part that is present approximately in the center or that matches the color of the previous pupil is the area of the pupil, and the pupil diameter can be measured.

The determination unit 7 is an element for determining whether the user has a brain disease using a pattern of time-dependent changes in the size of the pupil of the user photographed by the photographing unit, and the first pattern.

The determination unit 7 obtains the pupil size of the user over time, for example, based on the algorithm mentioned above. Then, the determination unit 7 analyzes the changing pupil for changes in the pupil size of the user for a certain period of time. For example, it is determined whether the pupil size of the user for a certain period of time tends to increase or decrease, and whether the amount of change is within a constant range. In this way, the determination unit can analyze changes in the pupil size of the user.

Moreover, the determination unit 7 determines the maximum and minimum values of the user's pupil for a certain period of time, and further determines the difference A between them. The pupil may be of the dominant eye or non-dominant eye, or of both of them. Then, either or both of a part within a certain range (e.g., a range of 0.2 mmA to 0.5 mmA) from the maximum value (upper part) and a part within a certain range (e.g., a range of 0.2 mmA to 0.5 mmA) from the minimum value (lower part) may be determined, and it may be examined whether there is a correlation between the frequency of appearance of either or both of the upper and lower parts and the first pattern. For example, when the lower part appears with the same frequency as the change frequency of the first pattern (or within a certain time gap), it may be determined that the user is a healthy person. In this process, pupil parts of the user are extracted by image analysis from an image photographed by the photographing unit. Then, the relative sizes of two pupil parts in the image are calculated and stored in the memory unit. The calculation unit reads the information on the sizes of the left and right pupils stored in the memory unit, and obtains their time-dependent changes. As a result, the control unit can analyze the time to give the maximum and minimum values of the pupil size, a time region in which the pupil size increases and a time region in which the pupil size decreases, and a time region in which the variation of the pupil size is in a constant range. In this way, it is possible to determine the maximum and minimum values of the pupil size, and the pattern of time changes in the pupil size.

In addition, if the correlation between the time-dependent changes in the user's pupil and the first pattern is low, it may be determined that the severity of brain disease is high. If the index, such as correlation coefficient, is within a certain range, it may be determined that the risk of developing the brain disease is high.

The pattern of time-dependent changes in the pupil size of the user preferably includes a pattern of time-dependent changes in the difference in the pupil size between the dominant eye and non-dominant eye. In this device, the dominant eye may be the eye with a larger average pupil size corresponding to a situation in which a bright screen is displayed after the change from a dark screen to the bright screen. The user makes a circle with the thumb and index finger of the hand, looks at a certain target with both eyes, and tries to get the target into the circle made by the hand. In that state, the user closes one eye and looks at the target with the open eye. The eye looking at the target in the circle may be used as the dominant eye. Conversely, the eye looking at the target out of the circle may be used as the non-dominant eye. In general, the pupil is smaller in the situation of viewing a bright screen. Therefore, it is possible to know whether the user is looking at a dark screen or a bright screen. On the other hand, there is a lag (time delay) of changes in the pupil size even when the screen changes; thus, in the pupil size corresponding to a situation in which a bright screen is displayed, there is a state in which the changes in the pupil diameter do not catch up with the change of the screen itself to a bright situation. When the screen itself changes from dark to bright situations, the pupil diameter changes from a large state to a small state for a while. The process of changes in the pupil is also included.

The computer may store various diseases and pupil changes corresponding thereto in the memory unit. Further, the computer may photograph changes in the pupil of a plurality of patients for a plurality of diseases, machine-learn the diseases and time-dependent changes in the pupil, and construct a database for the diseases and the time-dependent changes in the pupil. As a result, the determination unit 7 can determine time-dependent changes in the user's pupil using an image including the user's pupil photographed by the photographing unit 5, and pattern the changes, thereby diagnosing whether the user has a brain disease, whether the brain disease is severe, and whether the risk of developing the brain disease is high.

It is preferable that this device further has an age memory unit 9 that stores the age information of the user. Then, the display image control unit 3 preferably controls the predetermined time pattern based on the age information of the user stored in the age memory unit. This is based on the experimental results that older users (subjects) are more likely to show abnormal responses to screen changes in a small number of seconds. For example, it is preferable to take control so that the time interval for switching the display is shorter for older users by multiplying the display interval time by the reciprocal of the user's age, which is used as a coefficient. Alternatively, at least for users above a certain age, it is preferable to prepare, in addition to a normal display mode, a short-time switching mode that switches the display in a short period of time. The computer reads the information on the user's age from the age memory unit, reads a threshold value from the memory unit, and compares the age and the threshold value. Then, if the user's age exceeds the threshold value, the device may be controlled in the short-time switching mode or to display at least the short-time switching mode as well. The device may further have an information processing unit 11 for performing various types of processing (e.g., machine-learning processing).

In the device for diagnosing a brain disease 1, the display image control unit 3 changes a display image displayed on a display unit based on a previously stored first pattern.

Then, the photographing unit 5 photographs the pupil of a user who visually recognizes the display image.

The determination unit 7 receives an image including the user's pupil photographed by the photographing unit 5. Then, the determination unit 7 obtains a pattern of time-dependent changes in the size of the pupil of the user photographed by the photographing unit, and determines whether the user has a brain disease using the pattern of time-dependent changes and the first pattern. The determination unit 7 is preferably configured to be able to further diagnose, for example, whether the brain disease is severe or whether the risk of developing the brain disease is high. This device is preferably a device for diagnosing a brain disease that diagnoses the brain disease according to a machine-learning prediction algorithm. Data on time-dependent changes in the pupil for individual brain diseases are input into a system. Then, the correlation between each disease, the pattern of time-dependent changes, and the first pattern can be analyzed by machine-learning the various input data. In this way, the machine-learning prediction algorithm can be obtained. Then, the machine-learning prediction algorithm can be used to diagnose each brain disease. The pattern of changes in the pupil diameter for each disease can be learned through repeated machine learning, and individual brain diseases can be predicted.

This specification also provides a program that allows a computer to function as:

means configured to change a display image displayed on a display unit based on a first pattern;

means configured to receive a photographic image of the pupil of a user who visually recognizes the display image, the photographic image being photographed by a photographing unit; and means configured to obtain a pattern of time-dependent changes in size of the pupil of the user photographed by the photographing unit using the received photographic image of the pupil, and to determine whether the user has a brain disease using the obtained pattern of time-dependent changes in the pupil size, and the first pattern.

This program may also allow a computer to further realize each function of the device for diagnosing a brain disease described above.

This specification also provides a program that allows a computer to perform:

a step of changing a display image displayed on a display unit based on a first pattern;

a step of receiving a photographic image of a pupil of a user who visually recognizes the display image, the photographic image being photographed by a photographing unit; and a step of obtaining a pattern of time-dependent changes in size of the pupil of the user photographed by the photographing unit using the received photographic image of the pupil, and determining whether the user has a brain disease using the obtained pattern of time-dependent changes in the pupil size, and the first pattern.

This program may also allow a computer to further realize each function of the device for diagnosing a brain disease described above.

This program can be installed, for example, on a portable terminal, such as a smart phone, or on a game machine to provide a simple brain diagnosis tool using the smart phone or the like.

This specification may be an information recording medium that stores the above program and that can be read by a computer. Examples of information recording media include CD-ROMs, DVDs, and memory sticks.

EXAMPLE 1

The present invention will be described in detail below using Examples. The present invention is not limited to the following Examples.

A computer was set so that a monitor displayed a white screen and a black screen every three seconds after the start of the experiment. Further, a camera was prepared to photograph the pupil of a target. In addition, a program was designed to analyze changes in the pupil of the target from photographic images. This example was configured to be able to obtain the absolute size of the pupil diameter of the target.

Figure 3:
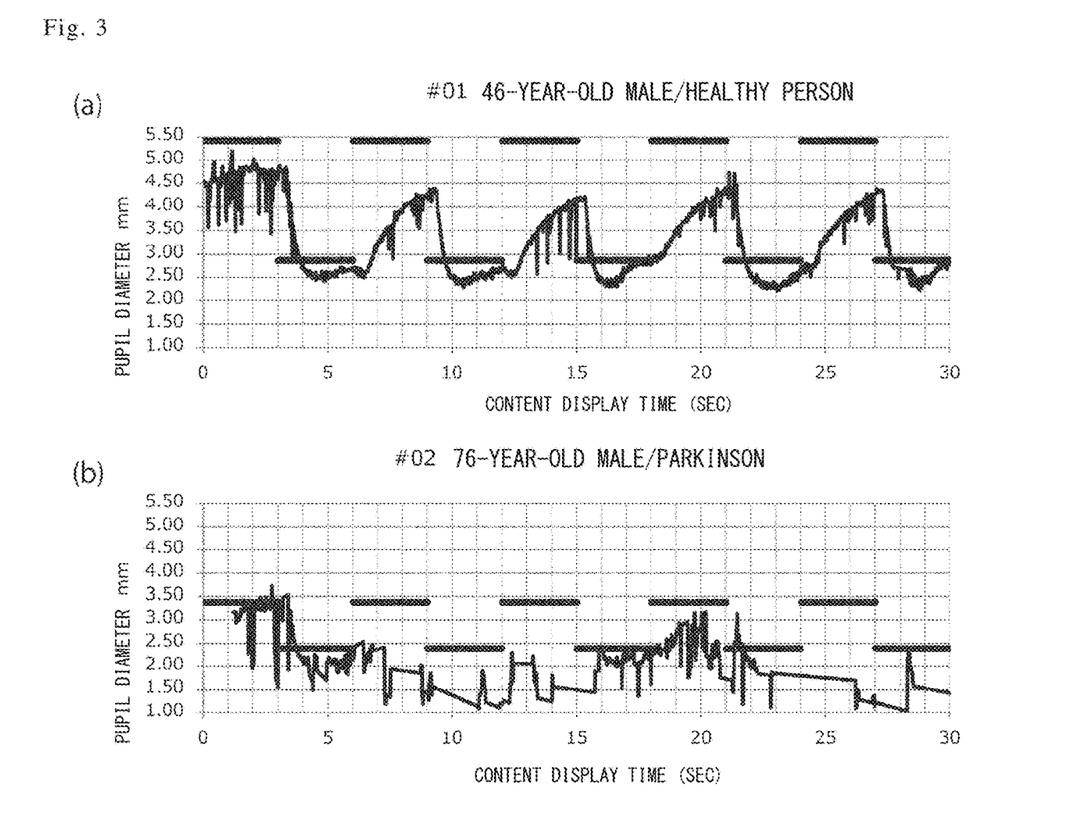
FIG. 3 shows graphs that replace drawings showing pupil changes and pattern changes in an Example.

FIG. 3 shows graphs that replace drawings showing pupil changes and pattern changes in the Example. FIG. 3(a) is a conceptual diagram showing pupil changes in a healthy person and a pattern display. On the other hand, FIG. 3(b) is a conceptual diagram showing pupil changes in a patient with Parkinson's disease and a pattern display.

FIG. 3(a) reveals that in the healthy person, there is a correlation between the changes in the display pattern and the time-dependent changes in the pupil diameter (the pupil diameter changes at a period of approximately every 3 seconds).

FIG. 3(b) reveals that in the patient with Parkinson's disease, there is no correlation between the changes in the display pattern and the time-dependent changes in the pupil diameter. In the graphs, the vertical axis shows the pupil diameter, and the horizontal axis shows the time.

EXAMPLE 2

There is always some difference between the left and right pupil diameters. The experimental results revealed that statistically, the possibility of developing a specific disease was higher when this difference was larger. Further, the experimental results revealed that statistically, the pupil diameter decreased with age (the older people had smaller normal pupil diameters; there was less amplitude). It was estimated that the pupil diameter of the dominant eye was generally larger. The dominant eye reaches first when looking at a certain object, and the non-dominant eye follows to view the object stereoscopically later. It was assumed that the dominant eye was the one with a larger average pupil value when looking at a bright screen from a dark screen in the basic pupil value determination. The experimental results revealed that patients with specific brain diseases showed abnormal changes in short time in the autonomic nerves, "sympathetic nerves (mydriasis, dark screen) and parasympathetic nerves (miosis, bright screen)," which control the pupil diameter during changes in light adaptation time and dark adaptation time. It was also revealed that the older the age was, the more likely abnormal responses to screen changes in short time appeared.

When comparing the data of many people, basic pupil values are obtained, which are considered to be comparable data.

In changes in the dominant eye and non-dominant eye (difference in following the gaze position), and the combination of the time of viewing blight and dark screens with the dominant eye and non-dominant eye and changes in the pupil diameter, when the difference from the average value of healthy persons is large, it can be determined that there is abnormality (a specific disease is developed). Individual examination reveals analysis result patterns of specific diseases.

Regarding the difference in the size between the left and right pupils, in view of previous experiments, the causative nervous system diseases include diseases of the cerebral nerves as well as abnormalities in some parts of the sympathetic or parasympathetic nervous system (autonomic nervous system). Examples of brain diseases include stroke and cerebral hemorrhage (spontaneous hemorrhage or hemorrhage due to head injury), as well as specific tumors or infections, although their statistical frequency is low. Non-brain diseases that affect the sympathetic nervous system include tumors or injuries of the neck or upper chest. Horner's syndrome is a combination of three symptoms: constriction of the pupil, drooping of the eyelids, and decreased sweating around the abnormal eye. Regardless of the cause, Horner's syndrome is caused by a split in the sympathetic nervous system connected to the eye.

Figure 4:
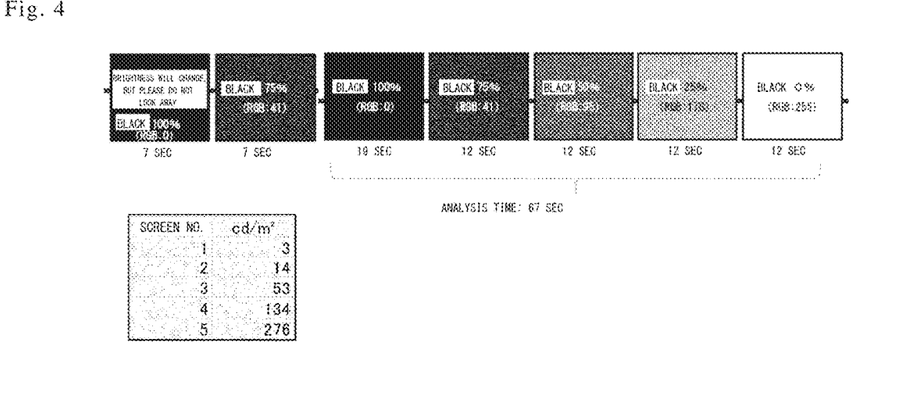
FIG. 4 is a conceptual diagram showing a control example of a display screen for obtaining basic pupil values.

FIG. 4 is a conceptual diagram showing a control example of a display screen for obtaining basic pupil values. In this example, at first, an initial message "brightness will change, but please do not look away" is displayed, and screens of various colors are displayed for a predetermined period of time. The percentage of darkness varies from 100%, 75%, 100%, 75%, 50%, 25%, and 0%. The display times after the initial display are 7 seconds (initial display), 7 seconds, 19 seconds, 12 seconds, 12 seconds, 12 seconds, and 12 seconds.

Figure 5:
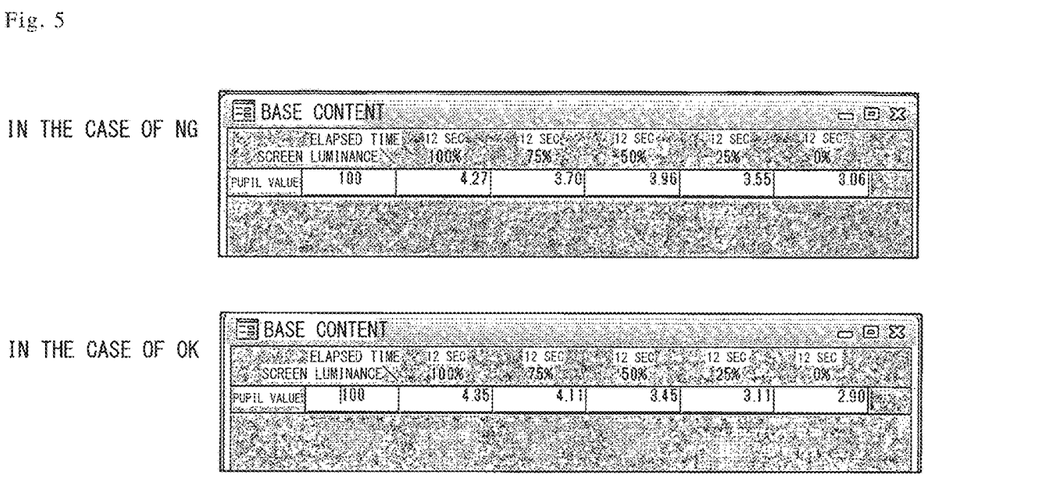
FIG. 5 shows an example of failure (NG; upper figure) and an example of success (OK; lower figure) in obtaining basic pupil values.

FIG. 5 shows an example of failure (NG; upper figure) and an example of success (OK; lower figure) in obtaining basic pupil values.

In the example of the upper figure, the pupil diameter at 50% darkness is larger than that at 75% darkness; thus, it is determined to be an abnormal value. That is, the control unit stores the degree of darkness of each pattern and the measured pupil diameter value of the user. Then, the pupil diameter values are compared for each darkness pattern value. If some of the pupil diameter values are large when the darkness value is small (luminance is high), it is determined to be abnormal. Then, it is output that there is abnormality, and detection is carried out again. In the case of success, the values of the maximum and minimum pupil diameters can be obtained using the case at 100% luminance and the case at 0% luminance. The obtained values of the maximum and minimum pupil diameters are stored in the memory unit as appropriate and can be used for later analysis. Basic pupil values may be obtained and may be analyzed; or instead of obtaining basic pupil values, the pupil value obtained on the spot may be used to analyze the presence or absence of developing brain disease.

EXAMPLE 3

Figure 6:
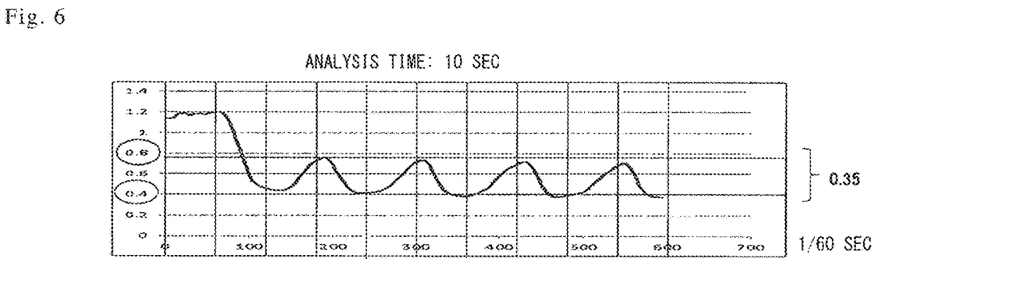
FIG. 6 is a graph that replaces a drawing showing changes in the pupil diameter when black and white are displayed every second and changes in the pupil diameter are measured.

Black and white were displayed every second for a user, who was a healthy person, and changes in the pupil diameter were measured. The results are shown in FIG. 6. FIG. 6 is a graph that replaces a drawing showing changes in the pupil diameter when black and white are displayed every second and changes in the pupil diameter are measured. FIG. 6 reveals that the changes in the pupil diameter of the healthy person are periodic and stable.

EXAMPLE 4

Figure 7:
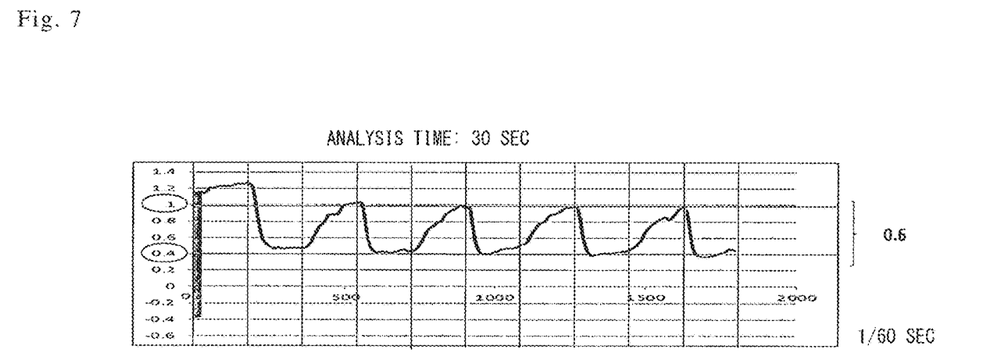
FIG. 7 is a graph that replaces a drawing showing changes in the pupil diameter when black and white are displayed every three seconds and changes in the pupil diameter are measured.

Black and white were displayed every three second for a user, who was a healthy person, and changes in the pupil diameter were measured. The results are shown in FIG. 7. FIG. 7 is a graph that replaces a drawing showing changes in the pupil diameter when black and white are displayed every three seconds and changes in the pupil diameter are measured. FIG. 7 reveals that the changes in the pupil diameter of the healthy person are periodic and stable.

EXAMPLE 5

Figure 8:
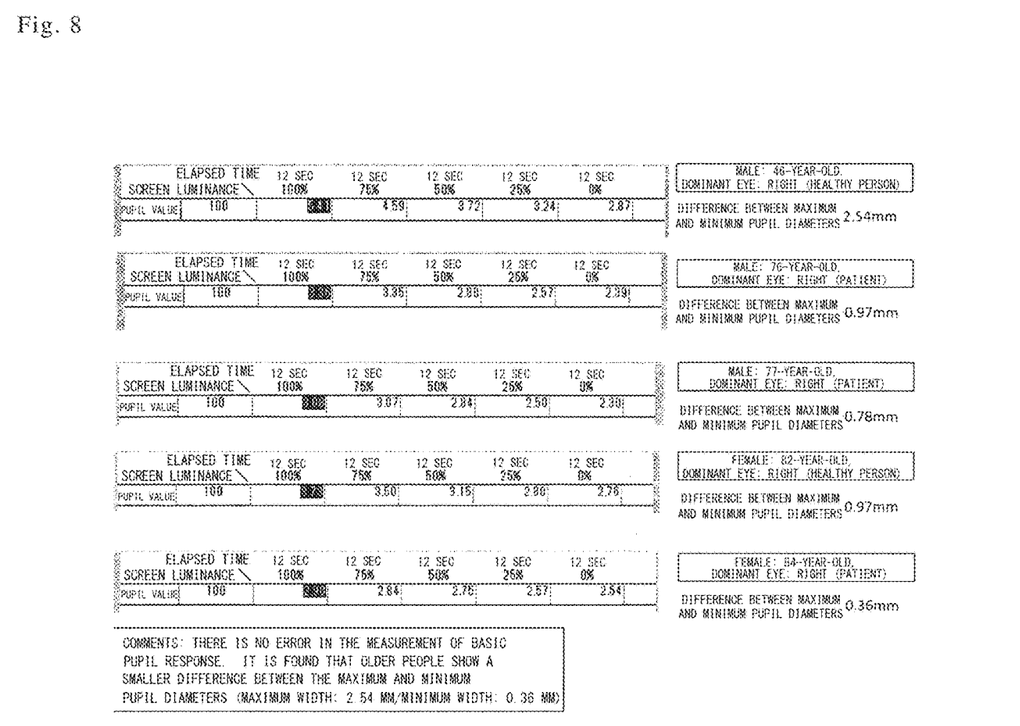
FIG. 8 shows the measurement results of the difference between the maximum and minimum pupil diameters.

For a plurality of persons, the difference between the maximum and minimum pupil diameters was determined. FIG. 8 shows the measurement results of the difference between the maximum and minimum pupil diameters. FIG. 8 reveals that the difference between the maximum and minimum pupil diameters decreases with increasing age. This suggests that multiple differences between the maximum and minimum pupil diameters of healthy persons of a certain age are obtained and stored in the memory unit, and the stored differences are read to calculate statistical values, such as average value and variance, whereby it is possible to determine the reference value of the difference at the certain age. Further, it is found that the above difference of the patients with brain-related diseases is smaller than that of the healthy persons.

For this reason, it may be determined whether the user is at the risk of having a brain-related disease by reading the reference value of the difference at a certain age, the user's age information, and the measured difference from the memory unit, and comparing the reference value of the difference at the user's age and the value of the measured difference. In this case, for example, if the above measured value is less than or equal to a predetermined percentage of the above reference value, it may be determined that the user is at the risk of having a brain-related disease. In this case, the numerical value for the predetermined percentage is stored in the memory unit, the measured difference of the user, the reference value at the user's age, and the numerical value for the predetermined percentage are read, the ratio of the measured difference of the user to the reference value at the user's age is determined, and a calculation is made to compare this ratio with the numerical value for the predetermined percentage, whereby it can be determined whether the user is at the risk of having a brain-related disease. On that basis, using the time-dependent changes in the pupil diameter, whether the user has a brain-related disease, and the severity of the disease may be reconsidered.

EXAMPLE 6

Changes in the pupil diameter were measured when black and white screens were displayed alternately every second for 30 seconds.

Figure 9:
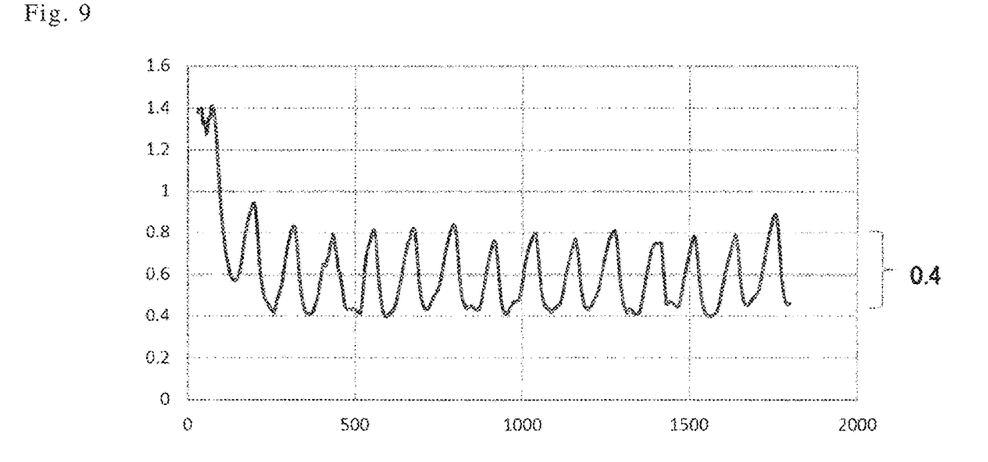
FIG. 9 is a graph that replaces a drawing showing pupil changes in a healthy person.

FIG. 9 is a graph that replaces a drawing showing pupil changes in a healthy person. FIG. 9 shows pupil changes in the first 46-year-old male (healthy person) in FIG. 8.

Figure 10:
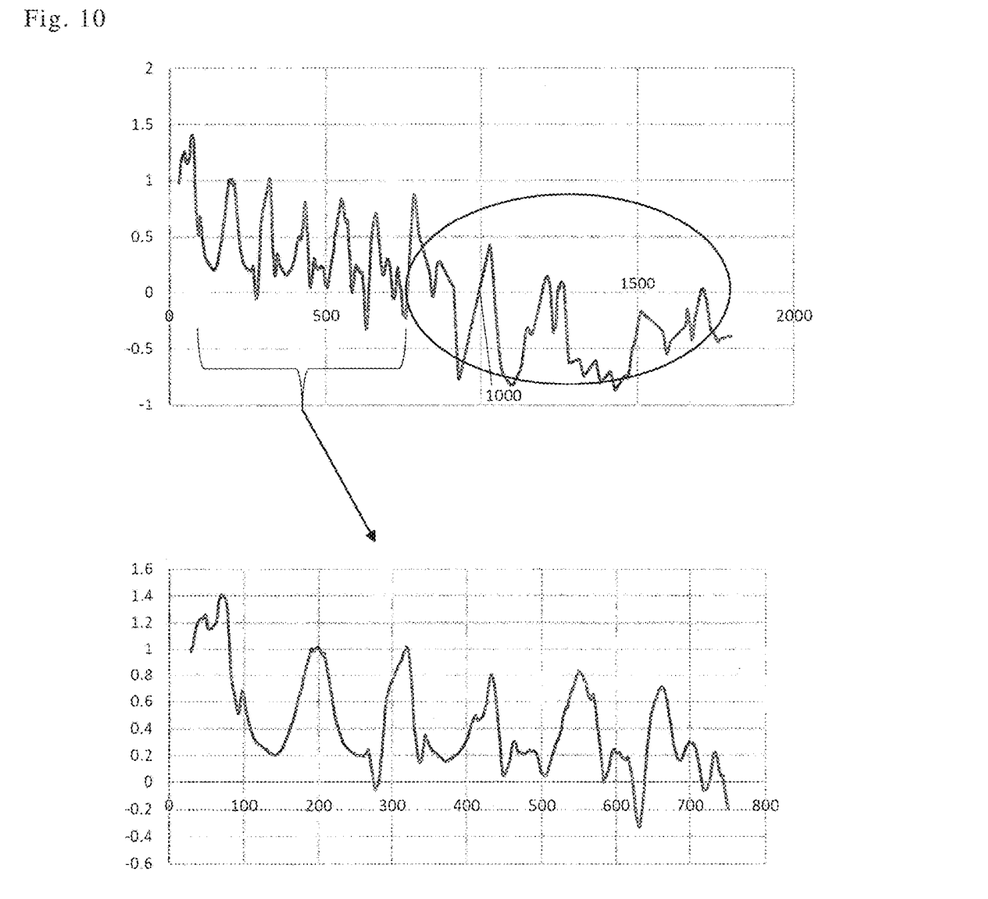
FIG. 10 is a graph that replaces a drawing showing pupil changes in a patient with a brain disease.

FIG. 10 is a graph that replaces a drawing showing pupil changes in a patient with a brain disease. FIG. 10 shows pupil changes in the second 76-year-old male (patient) in FIG. 8. In the example shown in FIG. 10, the pupil diameter changed relatively periodically at the beginning of the measurement (lower enlarged figure); however, in the latter half of the measurement, the changes in the pupil diameter were not periodic. Therefore, it was found that the timing of periodicity collapse (pattern of time-dependent changes in the pupil diameter) varied with specific diseases. It was also found from this Example that to diagnose all the brain-related diseases, it was preferable to perform pattern display, for example, for 10 seconds or more (10 seconds or more and 10 minutes or less, 15 seconds or more and 5 minutes or less, or 15 seconds or more and 3 minutes or less), and to continue to measure the pupil diameter.

FIG. 11 shows graphs that replace drawings showing pupil changes. The upper graph of FIG. 11 shows pupil changes in the third 77-year-old male (patient) in FIG. 8. The center graph of FIG. 11 shows pupil changes in the fourth 82-year-old female (healthy person) in FIG. 8. The lower graph of FIG. 11 shows pupil changes in the fifth 84-year-old female (patient) in FIG. 8. As shown in FIG. 11, the pupil changes in the healthy person are periodic and stable. On the other hand, the pupil changes in the patients reflect the pattern of the developing disease, and there are non-periodic changes.

INDUSTRIAL APPLICABILITY

This invention can be used as a medical equipment, and can also be used as a mobile terminal application.

REFERENCE SIGNS LIST

1. Device for diagnosing brain disease
3. Display image control unit
5. Photographing unit
7. Determination unit
11. Age memory unit

The invention claimed is:

1. A device for diagnosing a brain disease, comprising:
   a display image controller that comprises a processor, wherein the processor is configured to change a display image which is a digital image and is displayed on a display unit based on a first pattern that varies based on a predetermined time pattern;
   a photographing unit that is configured to photograph a pupil of a user who visually recognizes the display image and obtain a digital information which relates to the pupil of the user;
   a determination unit that is configured to analyze a pattern of time-dependent changes in size of the pupil of the user using the digital information which relates to the pupil of the user and which is configured to determine whether the user has a brain disease using the pattern of time-dependent changes in size of the pupil of the user and the predetermined time pattern of the first pattern;
   a time-dependent change pattern input unit that receives a patient time-dependent change pattern as a pattern of time-dependent changes in pupil size of patients with various brain diseases; and
   a time-dependent change pattern machine-learning unit that machine-learns the pattern of time-dependent changes in the patients with various brain diseases based on the patient time-dependent change pattern,
   wherein the determination unit determines whether the user has a target brain disease based on the pattern of time-dependent changes in the patients with various brain diseases machine-learned by the time-dependent change pattern machine-learning unit.

2. The device for diagnosing a brain disease according to claim 1, wherein
   the first pattern is one or two or more of luminance, color, and lightness that vary based on the predetermined time pattern.

3. The device for diagnosing a brain disease according to claim 2, further comprising
   an age memory unit that stores age information of the user, wherein
   the display image controller that controls the predetermined time pattern based on the age information of the user stored in the age memory unit.

4. The device for diagnosing a brain disease according to claim 1, wherein
   the first pattern is a white screen and a black screen that change periodically.

5. The device for diagnosing a brain disease according to claim 1, wherein
   when there is a correlation between the pattern of time-dependent changes in the pupil size of the user and the predetermined time pattern of the first pattern, the user is determined to be a healthy person.

6. The device for diagnosing a brain disease according to claim 1, wherein
   the pattern of time-dependent changes in the pupil size of the user includes a pattern of time-dependent changes in the difference of the pupil size between a dominant eye and a non-dominant eye.

7. The device for diagnosing a brain disease according to claim 1, wherein
   the brain disease is epilepsy, neurodegenerative disease, neural stem cell disease, neural progenitor cell disease, ischemic disease, neurological trauma, affective disorder, neuropsychiatric disease, retinal degenerative disease, retinal injury/trauma, cognitive, learning and memory impairment, Alzheimer's disease, mild cognitive impairment (MCI), Parkinson's disease, parkinsonian syndrome, Huntington's disease, amyotrophic lateral sclerosis, ischemic stroke, traumatic brain injury, depression, bipolar depression/disorder, chronic fatigue syndrome, anxiety syndrome/disorder, autism, or Asperger's syndrome.

8. The device for diagnosing a brain disease according to claim 7, wherein
   the device diagnoses the brain disease according to a machine-learning prediction algorithm.

9. The device for diagnosing a brain disease according to claim 1, wherein the size of the pupil of the user is size of pupil diameter of the user.

\* \* \* \* \*